US00PP27833P2

(12) United States Plant Patent
Hansen

(10) Patent No.: US PP27,833 P2
(45) Date of Patent: Apr. 4, 2017

(54) ***BUDDLEIA* PLANT NAMED 'WISTERIA LANE'**

(50) Latin Name: ***Buddleia* hybrid (L.)**
Varietal Denomination: Wisteria Lane

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 148 days.

(21) Appl. No.: 14/545,723

(22) Filed: Jun. 10, 2015

(51) Int. Cl.
*A01H 5/00* (2006.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

| | | | |
|---|---|---|---|
| PP12,383 | P2 | 2/2002 | Dransfield |
| PP14,370 | P2 | 12/2003 | Turrell |
| PP17,332 | P2 | 1/2007 | Moore |
| PP19,934 | P2 | 4/2009 | Davis |
| PP19,935 | P2 | 4/2009 | Bloom |
| PP19,950 | P3 | 4/2009 | Werner |
| PP19,991 | P3 | 5/2009 | Werner |
| PP22,063 | P2 | 8/2011 | Valin |
| PP22,064 | P2 | 8/2011 | Valin |
| PP22,065 | P2 | 8/2011 | Podaras |
| PP22,066 | P2 | 8/2011 | Podaras |
| PP22,067 | P2 | 8/2011 | Podaras |
| PP22,068 | P2 | 8/2011 | Podaras |
| PP22,069 | P2 | 8/2011 | Podaras |
| PP22,080 | P2 | 8/2011 | Podaras |
| PP22,081 | P2 | 8/2011 | Podaras |
| PP22,098 | P2 | 8/2011 | Podaras |
| PP22,108 | P2 | 9/2011 | Podaras |
| PP22,109 | P2 | 9/2011 | Podaras |
| PP22,110 | P2 | 9/2011 | Podaras |
| PP22,142 | P2 | 9/2011 | Podaras |
| PP22,143 | P2 | 9/2011 | Podaras |
| PP22,144 | P2 | 9/2011 | Podaras |
| PP22,177 | P2 | 10/2011 | Podaras |
| PP22,367 | P2 | 12/2011 | Podaras |
| PP22,465 | P2 | 1/2012 | Brand |
| PP22,680 | P2 | 4/2012 | Senior |
| PP23,214 | P2 | 11/2012 | Moore |
| PP23,425 | P2 | 2/2013 | Werner et al. |
| PP23,461 | P2 | 3/2013 | Valin |
| PP23,462 | P2 | 3/2013 | Valin |
| PP23,463 | P2 | 3/2013 | Valin |
| PP23,464 | P2 | 3/2013 | Valin |
| PP23,498 | P2 | 3/2013 | Podaras |
| PP24,015 | P3 | 11/2013 | Werner |
| PP24,016 | P3 | 11/2013 | Werner |
| PP24,030 | P3 | 11/2013 | Podaras |

*Primary Examiner* — Susan McCormick Ewoldt
*Assistant Examiner* — Karen Redden

(57) ABSTRACT

*Buddleia* 'Wisteria Lane' is a short, multi-stemmed, arching or weeping mounded, winter-hardy butterfly bush plant with long, compact, arching flowering thyrse over a long season beginning mid-summer with sweetly-fragrant lavender flowers.

1 Drawing Sheet

Botanical classification: *Buddleia* hybrid (L.).
Variety denomination: 'Wisteria Lane'.

BACKGROUND AND ORIGIN OF THE PLANT

The present invention relates to the new and distinct, Butterfly Bush plant, *Buddleia* 'Wisteria Lane' was hybridized by the inventor in the summer of 2011 at a wholesale perennial nursery in Zeeland, Mich., USA. The new plant, originally labeled H11-34-01, is a single seedling selection from an open pollination of a proprietary hybrid HK10-212-01 (not patented) as the female or seed parent. The male parent is unknown but because the female parent was grown in a large population of selected hybrid plants the potential for variation was large.

*Buddleia* 'Wisteria Lane' was first asexually propagated in 2013 by stem cuttings at the same nursery in Zeeland, Mich. The resultant asexually propagated plants have been found to be stable and true to type in successive generations of asexual reproduction.

BRIEF SUMMARY OF THE PLANT

*Buddleia* 'Wisteria Lane' differs from its female parent as well as all other winter-hardy butterfly bush plants known to the applicant in many traits. The habit of 'Wisteria Lane' is uncommonly weeping or arching in both stem and thyrse. The foliage is silvery green and flower color is lavender. Compared to the proprietary female parent, HK10-212-01, 'Wisteria Lane' is much more arching or weeping habit in both stems and thyrse.

The nearest commercially available comparison plants include: *Buddleia* (FLUTTERBY FLOW™ Lavender)='Podaras #12' U. S. Plant Pat. No. 22,098 with similar flower color but shorter thyrse and habit that is shorter, more horizontal and less arching, 'Podaras #11' U.S. Plant Pat. No. 22,067 is taller, more rigid and upright. 'Lavender' BUZZ™ is taller, has a more upright habit with less arching or weeping and produces a much shorter and upright thyrse. Compared to 'Purple Haze' U.S. Plant Pat. No. 24,514 the new plant has flower color of much lighter purple and has a weeping or arching rather than spreading habit.

The following Table 1 further demonstrates some comparisons with the new plant and the nearest comparison cultivars.

TABLE 1

| CULTIVAR | LEAF COLOR | FLOWER COLOR | HABIT | SIZE (H × W) |
|---|---|---|---|---|
| 'Purple Haze' | medium green | deep purple | spreading | 120 cm × 120 cm |
| 'Lavender' BUZZ ™ | medium green | lavender | mounded | 120 cm × 165 cm |
| 'Podaras 11' | dark green | lavender | upright | 150 cm × 150 cm |
| 'Podaras #12' | silvery green | lavender | sprawling | 60 cm × 120 cm |
| 'Wisteria Lane' | silvery green | lavender | weeping | 105 cm × 160 cm |

*Buddleia* 'Wisteria Lane' is a distinct, winter-hardy, butterfly bush different from all other *Buddleia* cultivars known to the inventor based on the following combined traits:

1. Winter-hardy shrub, with multiple-stemmed, branched, short, weeping habit.
2. Tightly clustered salverform flowers on long, weeping thyrse on arching stems over a prolonged season beginning mid-summer.
3. Lavender flowers in long, dense, arching thyrse.
4. Elliptic to lanceolate foliage of silvery green with narrowly acute apex and attenuate base.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
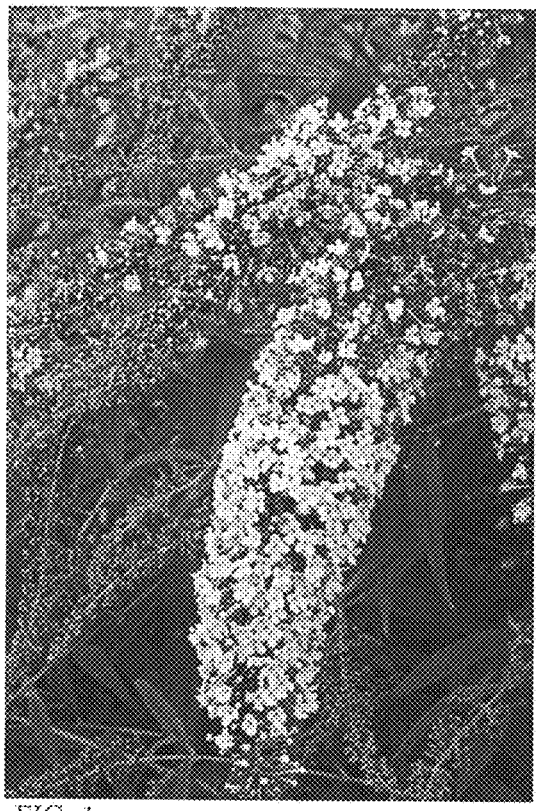
FIG. 1 shows a close-up of the flowers.
Figure 2:
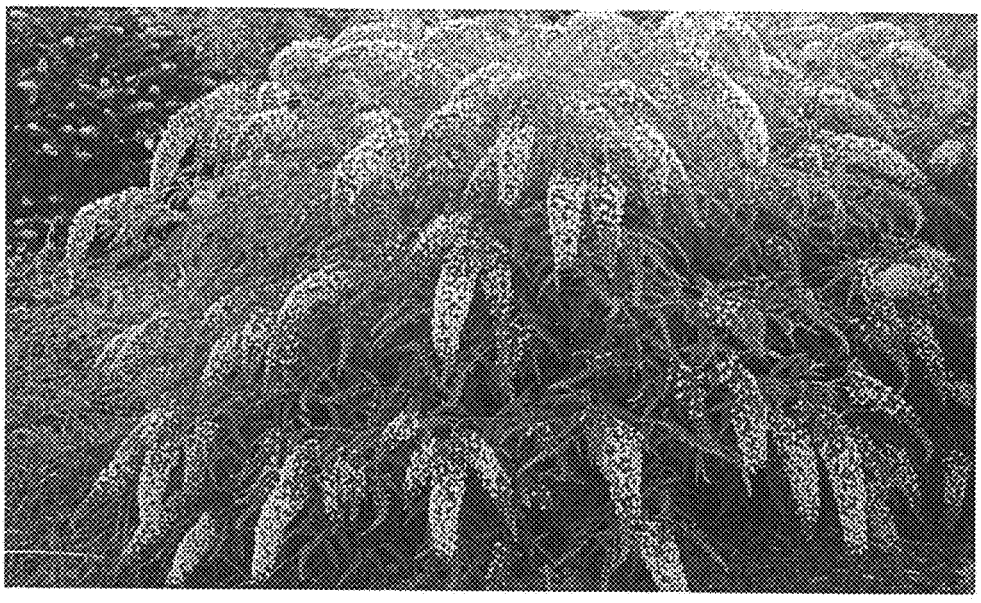
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Wisteria Lane', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand open-sun field trials of a nursery in Zeeland, Mich. with supplemental fertilizer and water as needed. The plants are, natural habit and were not treated with plant growth regulators, nor were they pinched at any time in the growth year.

Parentage: Unreleased proprietary hybrid # HK10-212-01 (not patented) as the female or seed parent as the female or pod parent times the an unknown open-pollination as the male or pollen parent.

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type; becoming woody to 1.5 cm diameter.

*Crop time*.—Under normal summer growing conditions 12 to 16 weeks to flower in a four-liter container from cutting. Plant vigor is very good.

Plant description:

*Plant shape and habit*.—Winter-hardy, herbaceous, semi-woody, well-branched shrub with about 24 thick upright and branched main stems producing an arching mound about 105 cm tall and about 160 cm wide.

*Stem*.—Glabrous and woody in lower portion, rounded in cross section with exfoliating bark; younger upper portion puberulent and quadrangular in cross section; strong, arching and very flexible; average about 36 cm tall from soil line to just below terminal flowers, and about 1.1 cm diameter at the base, average about 8.0 mm diameter; before distal flowers about 11 branches per main stem extending at about 60° angle from horizontal.

*Stem color*.—Just below flowers between RHS 193D and RHS 145D with undertone of between RHS 185C and RHS N187 more concentrated on portions receiving more sun exposure to nearly solid between RHS 184A and RHS 183D; and striated in about basal 15 cm with fissures of nearest RHS 165D and between RHS 165A and RHS 165B.

*Plant size*.—Unpinched plant with stems flowering to about 105 cm tall; overall plant about 160.0 cm wide.

*Internode*.—About 15 nodes per stem, average internode length about 3.8 cm on unpinched plant; upper nodes pubescent, lower nodes becoming glabrous.

*Node color*.—Same color as surrounding stem to slightly more tinted with RHS 184A.

Foliage description: Opposite, decussate; serrulate; puberulent abaxial and glabrous adaxial; elliptic to lanceolate with attenuate base and acute apex; no foliar fragrance detected.

*Leaf blade size*.—Up to about 14.5 cm long and about 3.5 cm wide, average about 12.5 cm long and about 3.0 cm wide; distally becoming smaller and more lanceolate.

*Foliage color*.—Young expanding leaf adaxial side between RHS 138C and RHS 138B and abaxial nearest RHS 192C; mature leaves adaxial between RHS 138B and RHS 138C and abaxial more green than RHS 192D and lighter than RHS 138D.

*Veins*.—Reticulate; abaxial raised, adaxial slightly impressed.

*Vein color*.—Young expanding adaxial nearest RHS N144D, abaxial nearest RHS 155B; mature main vein adaxial variable nearest RHS 145A, abaxial main vein between RHS 145D and RHS 145C; lateral veins on young abaxial and adaxial same as surrounding leaf tissue; lateral abaxial veins of mature leaves nearest RHS 137B; lateral adaxial veins of mature leaves nearest RHS 138A.

*Petioles*.—Glaucous and glabrous adaxial, pubescent abaxial; flatted partially top to bottom; average size about 1.0 cm long and about 2.0 mm wide at the point of attachment to stem.

*Petiole color*.—Adaxial margins nearest RHS 138B and center vein nearest RHS 192C, with undertones of nearest RHS 183D, abaxial nearest RHS 192D.

Inflorescence description: Glomerate thyrse consisting of about 1000 self-cleaning salverform flowers; to about 22.5 cm long and 6.0 cm wide, beginning in mid-July and continuing until late October in Michigan.

*Buds*.—Narrowly spatulate, apex rounded; one day prior to opening about 11.5 mm long and about 3.0 mm in diameter and 2.5 mm long in club; tube portion about 0.9 mm diameter and about 9.5 mm long.

*Bud color*.—Club nearest RHS 86C; tube between RHS N77B and RHS N77D.

*Sepals*.—Typically four, proximal two-thirds connate adpressed to corolla tube; narrowly acute apex; glabrous both adaxial and abaxial; margin entire, edentate; fused in about the basal 2.0 mm and split in about the terminal 1.5 mm; forming a corolla about 3.5 mm long and about 1.0 mm across; individually less than about 0.7 mm wide at point of fusion.

*Sepal color*.—Adaxial nearest RHS 138D, abaxial between RHS 138C and RHS 138D.

*Flowers fragrance*.—Pleasantly and distinctly sweet.

*Petals*.—Typically four; glabrous; fused into salver-form with typically straight cylindrical tube about 10.0 mm long and 1.0 mm diameter, and a flattened face about 8.5 mm across; petal blade rounded with crenate margin; blade to about 3.5 mm across and about 3.0 mm long from fused face to apex; center 2.5 mm of flattened face portion of blade fused.

*Petal color*.—Adaxial center between RHS 25B and RHS 24A in the tube surrounded by a thin irregular band of less than 0.5 mm width of between RHS 21D and RHS 20B; adaxial face blades nearest RHS N87D; abaxial tube between RHS N79D and RHS N77D and abaxial petal blades nearest RHS N88D.

*Gynoecium*.—Pistil: one; about 4.0 mm long. Style: short, round, glabrous; about 1.2 mm long and less than 0.5 mm diameter; color between RHS 138D and RHS 144D. Stigma: oblong, minutely puberulent; about 1.2 mm in long and less than 0.5 mm long; color nearest RHS 143A. Ovary: superior; globose; about 1.0 mm across at base and 2.0 mm tall; distally tapering to style; color between RHS 144A and RHS 144B.

*Androecium*.—Filaments: not produced or very short. Anthers: typically four; oblong; introrse; adnate to about mid-point of corolla tube; about 1.0 mm long and less than 0 5 mm wide; color between RHS 191B and RHS 191C. Pollen: abundant, globose, less than 0.1mm long; color nearest RHS 11D.

*Pedicel*.—Short, puberulent; about 2.0 mm long and about 0.5 mm diameter; color nearest RHS 138B.

*Peduncle*.—Quadrangular, pubescent, flexible and strong; to about 27.0 cm long.

*Peduncle color*.—Nearest RHS 138C with frequent tinting of nearest RHS 183A where exposed to heavy direct sun exposure.

*Fruit*.—Moderate fruit set; oblong with acute apex; glabrous, bi-valved, septicidal capsule; about 5.0 mm long and about 2.0 mm diameter.

*Fruit color*.—As maturing nearest RHS N177B; when mature and dehiscing between RHS 165B and RHS 165C;

*Seed*.—Elongated ellipse with sharply acute ends; less than about 2.0 mm long and about 0.1 mm diameter in center.

*Seed color*.—Nearest RHS 200A.

Disease resistance: Resistance to deer browsing has been observed. Further resistance beyond that of other known winter-hardy butterfly bush cultivars has not been noted. The plant grows best with plenty of moisture and adequate drainage, but is able to tolerate some drought when mature. Hardiness at least from USDA zone 6 through 10.

I claim:

1. A new cultivar of winter-hardy butterfly bush plant *Buddleia* plant named 'Wisteria Lane' as herein illustrated and described, suitable for potted plant culture, landscaping as a specimen or en masse or as cut flower purposes.

* * * * *